(12) United States Patent
Tobin

(10) Patent No.: US 7,074,834 B2
(45) Date of Patent: Jul. 11, 2006

(54) LONG ACTING, REVERSIBLE VETERINARY SEDATIVE AND ANALGESIC AND METHOD OF USE

(75) Inventor: Thomas Tobin, Lexington, KY (US)

(73) Assignee: University of Kentucky Foundation, Lexington, KY (US)

( * ) Notice: Subject to any disclaimer, the term of this patent is extended or adjusted under 35 U.S.C. 154(b) by 0 days.

(21) Appl. No.: 09/865,175

(22) Filed: May 24, 2001

(65) Prior Publication Data

US 2002/0091161 A1 Jul. 11, 2002

Related U.S. Application Data

(60) Provisional application No. 60/206,625, filed on May 24, 2000.

(51) Int. Cl.
*A61K 31/155* (2006.01)
(52) U.S. Cl. ...................................... 514/634; 514/398
(58) Field of Classification Search ................ 514/634, 514/398, 183, 315, 462, 452
See application file for complete search history.

(56) References Cited

U.S. PATENT DOCUMENTS

| | | |
|---|---|---|
| 4,060,640 A | 11/1977 | Kodama et al. |
| 4,742,054 A | 5/1988 | Naftchi |
| 4,950,648 A | 8/1990 | Raddatz et al. |
| 5,635,204 A * | 6/1997 | Gevirtz et al. .............. 424/449 |
| 5,942,241 A | 8/1999 | Chasin et al. |
| 5,958,933 A | 9/1999 | Naftchi |

OTHER PUBLICATIONS

MEDLINE AN 20000025586, Veveris et al, Brit. J. Pharmacol, 128 (5), 1089-97, Nov. 1999, abstract.*
Veterinary Pharmacology and Therapeutics, Adams, pp. 160-161, 1995.*
Guanabenz (Wytensin), Prescription Drug Referene from Health Square.com, May 18, 2001.

* cited by examiner

*Primary Examiner*—Christopher S. F. Low
*Assistant Examiner*—Amy Lewis
(74) *Attorney, Agent, or Firm*—King & Schickli, PLLC

(57) ABSTRACT

A veterinary composition comprising a guanidine derivative, e.g., guanabenz or guanabenz acetate is provided which produces a rapid acting and long lasting sedative and analgesic effect in a subject animal that is selectively reversible. The use of guanabenz in the horse provides for a safe, effective, long lasting and rapidly reversible sedative and analgesic which can be used on the standing animal. Methods of use of the compositions of the invention are also provided.

15 Claims, 2 Drawing Sheets

LONG ACTING, REVERSIBLE VETERINARY SEDATIVE AND ANALGESIC AND METHOD OF USE

This application claims the benefit of priority in U.S. Provisional Application Ser. No. 60/206,625, filed on May 24, 2000.

FIELD OF INVENTION

The present invention relates to the field of veterinary medicine and to compositions and methods of use for rapid acting reversible sedatives, tranquilizers and analgesics in animals. In particular, the present invention relates to a rapid acting reversible sedative and analgesic having α adrenergic agonist activity that is adapted for use in the standing animal.

BACKGROUND OF THE INVENTION

Veterinary medicine and especially in large animal practice, e.g., equine and bovine medicine and surgery, has incorporated various diagnostic, therapeutic and surgical procedures into the daily routine of the large animal practitioner. Many of these procedures are greatly facilitated and can be accomplished in the standing animal if the animal remains clam, motionless, and virtually pain free. An additional consideration is that it may also be beneficial to calm the animal, e.g., the cow or horse, before bringing it into proximity of expensive equipment or to minimize the potential for human injury.

Commonly used are sedatives which have a calming effect and tranquilizers which are a class of drugs used in the treatment of anxiety states. The goal of sedative and tranquilizer administration is to eliminate fear, produce a calming effect, reduce resistance to manipulation, and, to the extent there is an analgesic effect of the drug, to ideally eliminate pain. Generally, users or user facilities of such sedatives, tranquilizers and analgesics are veterinary hospitals, veterinarians working under field conditions, animal control facilities, humane societies, zoos, researchers and the like.

Classically, sedatives are a distinct groups of drugs based on their central nervous system (CNS) site of action. Sedatives are classically considered as agents that act at the cortical level and, if given in sufficient quantities, will produce CNS depression to the point of hypnosis (artificial sleep). Tranquilizers act at the sub-cortical levels, particularly at the reticular activating system, effectively filtering afferent and efferent nervous system activity. Increasing doses of tranquilizers produce greater degrees of calming but do not produce hypnosis. In practical use in animals, drugs acting at different levels of the CNS have been used to obtain the same result, thus the distinction often has become blurred and the term sedative-tranquilizer has evolved.

Alpha-2-adreno receptor agonists produce sedation, muscle relaxation and analgesia when administered intravenously or intramuscularly. Alpha-2-adreno receptor agonists are used to provide standing chemical restraint for various procedures, to provide analgesia, and to act as sedatives prior to anesthesia. The most commonly used alpha-2-agonists used, e.g., in the horse, are xylazine, detomidine and romifidine. All produce dose-dependent sedation and muscle relaxation whereas only xylazine and detomidine possess analgesic properties. The duration of action of these alpha-2-adreno receptor agonists, however is typically short, e.g., a single intravenous administration of 300 mg of xylazine in an adult horse produces moderate sedation and analgesia lasting from between about 30 to about 60 minutes. Therefore, there exists a need in the art for a long acting sedative and analgesic which can produce profound sedation and analgesia for longer periods of time following a single administration of the active.

Upon administration of the alpha-2-agonists, horses typically assume a wide stance with the head extended and lowered (ptosis). In male horses, some relaxation of the penis may occur and the lower lip becomes flaccid. Muscle relaxation and ataxia may be severe, particularly when large doses are administered. The effects of alpha-2-adreno receptor agonists can be specifically antagonized (reversed) by the administration of and alpha-2-adreno receptor antagonist (Hubbell J. A. E. and Muir W. W. Standing Chemical Restraint p. 187–192 in Equine Internal Medicine by Reed S. M and Bayly W. M, 1997)

Central alpha-2-adrenergic agonist cross the blood-brain barrier and stimulate alpha-2-adrenergic receptors in the vasomotor region of the brainstem. Stimulation Of these receptors decreases sympathetic tone, brain turnover of norepinephrine and central sympathetic outflow and activity of the preganglionic sympathetic nerves. The net effect is a reduction in norepinephrine release. Central alpha-2-adrenergic agonist may also stimulate the peripheral alpha-2-adrenergic receptors that mediate vasoconstriction. The usual physiologic effect is a decrease in peripheral resistance and slowing of the heart rate; however, output is either unchanged or mildly decreased. Preservation of cardiovascular reflexes prevents postural hypertension.

In human medicine, a variety of guanidine derivatives have been used clinically as anti-hypertensive agents, including clonidine, guanabenz, guanacline, guanadrel, guanazodine, guanethidine, guanfacine and guanochlor, guanoxabenz and guanoxan.

Guanabenz (1-[2,6-dichlorobenzylidine-amino]-3-guanidine) is an anti-hypertensive drug whose mechanism of action is an agonistic stimulatory effect of the central alpha-2 adrenergic receptors in the cardiovascular regulatory centers in the brainstem and spinal cord. Its therapeutic effects in humans include a reduction in sympathetic tone (a reduction in heart rate and cardiac output), an increase in parasympathetic tone (a reduction in heart rate and cardiac output) and vasodilation (a relaxation of capacitance vessels and reduction in total peripheral resistance). Guanabenz is currently marketed in human medicine in the general class of medicines called antihypertensives. It is used to treat high blood pressure (hypertension). Guanabenz acetate is available on the market as 4 and 8 mg tablets to be taken orally, e.g., as WYTENSIN® (Wyeth-Ayerst, Alexandria, Va.)

Certain uses of guanabenz have been previously disclosed in the art. For example, U.S. Pat. No. 4,060,640, to Kodama et al., describes guanabenz, and its related compounds, as being central nervous system depressants that reduce hyperexcitability and induce sedation, overcoming psychic depression in humans.

U.S. Pat. No. 5,958,933 to Naftchi discloses guanabenz, as part of a drug combination, as being a neurologically active compound that when administered in an appropriate dosage amount is sufficient to restore neurological function or control spasticity in humans suffering from injury to the central nervous system.

U.S. Pat. No. 4,742,054 to Naftchi discloses guanabenz to have a restorative effect on the central nervous system, especially in the treatment in mammals of motor and sensory functional losses due to the traumatic injury to the spinal cord. Guanabenz is described as being an effective anaesthetic compound and for use in a method for treating a mammal having a damaged central nervous system.

U.S. Pat. No. 5,635,204 to Gevirtz et al. discloses guanabenz, in combination with other drugs at a particular dosage as being an effective anaesthetic.

U.S. Pat. No. 5,958,933, to Naftchi describes oral overdosage of guanabenz, as not being reported to result in anesthesia; the incidents were recorded as hypotension, somnolence, lethargy, irritability, myosis and bradycardia in young children.

In veterinary medical applications, equine racetrack veterinarians have previously used an 8 mg tablet of guanabenz, crushed and dissolved in water, and injected the resultant solution intravenously into horses prior to racing. The rationale behind this administration is that it reduces the blood pressure in the horse's pulmonary circulatory tract and thereby reduces the incidence and/or severity of exercise induced pulmonary hemorrhage (EIPH) in the horse.

Current available sedatives and tranquilizers such as the aforementioned xylazine and detomidine can produce side effects such as sinus bradychardia and first or second degree atrioventricular block (Bohart G. Anesthesia of Horses in the Field in Current Therapy in Equine Medicine by Robinson N. E, 1998.). Therefor there exists a need in the art for a safe, effective oral, intravenous, or intramuscular compound for the standing sedation, tranquilization and analgesic effect of larger mammals that does not produce the adverse side effects seen with current sedatives/tranquilizers.

Prior to the present invention guanidine derivatives, and in particular guanabenz and its analogs, have not been reported as useful as a standing sedative, tranquilizer and analgesic combination when used in horses and lower mammals at certain dosages.

OBJECTS OF THE INVENTION

Accordingly, it is an object of the invention to provide a veterinary composition in unit dosage form comprised of a guanidine derivative, e.g., guanabenz acetate, for administration to animals for the induction of a rapid onset and long lasting sedation and analgesia in the subject animal the effects of which are capable of being selectively reversed.

Another object of the invention, is to provide a method of producing a rapid onset and long lasting sedation and analgesia in an animal by administering in a single dose a pharmaceutically effective amount of a composition comprised of a guanidine derivative, e.g., guanabenz acetate, to the subject animal.

In particular, one object of the invention is to provide a composition and method for producing a rapid onset of sedation and analgesia in a standing animal, e.g., a large animal such as a horse, cow, sheep, pig, goat or the like that is selectively reversible.

Likewise, another object of the invention is to provide a novel veterinary composition comprised of a derivative of the guanidine family of compounds, wherein said derivative possesses α adrenergic receptor agonist activity, e.g., guanabenz acetate, for administration to animals for the induction of a rapid onset sedation and analgesia in the subject animal the effects of which are capable of being selectively reversed.

In particular, one object of the invention is to provide a composition and method for producing a rapid onset and long lasting sedation and/or analgesia in an animal which is selectively reversible.

Another object of the invention is to provide a novel veterinary composition comprising an α adrenergic receptor agonist, e.g., a guanidine derivative, and method of use comprising a single administration of a pharmaceutically effective amount of said composition to thereby produce a rapid onset and longer lasting sedation and/or analgesia in a standing large animal than is currently available to the veterinary medical profession and which has selective reversibility.

A further object of the invention is to provide a novel veterinary composition comprised of an α adrenergic receptor agonist, e.g., a guanidine derivative, and method of use comprising a single administration of a pharmaceutically effective amount of said composition to thereby produce a rapid onset and longer lasting means for chemical restraint in a standing large animal than is currently available to the veterinary medical profession and which has selective reversibility.

DETAILED DESCRIPTION OF THE INVENTION

Figure 1:
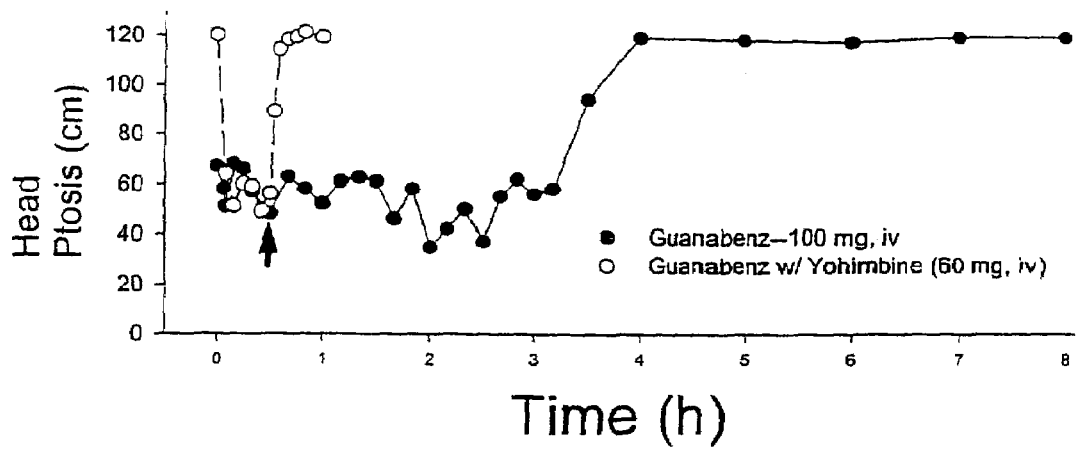
FIG. 1 is a plot of head ptosis response in a horse administered intravenous guanabenz (100 mg, 0.2 mg/kg)

The present invention relates to a new veterinary medical use for guanidine derivatives, e.g., guanabenz and/or guanabenz acetate (an anti-hypertensive drug used in humans to control high blood pressure), wherein the invention provides compositions thereof for producing a sedative, tranquilizer and analgesic effect in primarily horses but also in other animal species. Thus, the present invention relates generally to novel compositions and methods of use for the guanidine family of compounds (guanidine derivatives), e.g., guanabenz and guanabenz acetate, in providing a sedative, tranquilizer and analgesic effect not only in horses but also lower mammals by, e.g., intravenous injection of the aqueous solution of guanabenz or a derivative thereof into the subject animal.

As set forth in the teachings herein, guanabenz and the related guanidine derivatives that possess α adrenergic receptor agonist effects have utility as safe, effective, long lasting and rapidly reversible sedatives and/or tranquilizers and/or analgesics in other domestic animal species including but not limited to bovines, ovines, canines, and felines and other mammalian and domestic animal species requiring long acting, safe effective and rapidly reversible sedation and/or tranquilization and/or analgesia.

Additional objects, advantages and other novel features of the invention will be set forth in part in the description that follows and in part will become apparent to those skilled in the art upon examination of the foregoing or may be learned with the practice of the invention. Certain patents and printed publications are cited throughout the instant specification. The contents of these cited patents and printed publications are hereby incorporated herein in their entirety by reference.

As used herein by "rapid onset" is meant to include the time interval from administration of the active, e.g., guanabenz acetate, until the drug begins to take effect and produce the intended response, e.g., sedation and/or tranquilization and/or analgesia. For the compositions disclosed herein, this time interval typically ranges from between about 1 minute to about 30 minutes. As one of skill in the art can appreciate, the length of time for onset of action can vary, e.g., depending upon the route of administration, the species, age, size, and health status of the animal and the like. In the adult horse, for example, the clinical signs of sedation will begin to appear within 1–3 minutes following a single intravenous administration of about 100 mg of guanabenz or guanabenz acetate.

Likewise, by "sedation" is generally meant the act or process of calming or quieting an animal and may, in some instances be used synonymously with the term "tranquilization." The term "tranquilization" as used herein generally means the act or process of depressing the function of the central nervous system, relieving anxiety and inducing a state of calmness in the conscious animal.

The term "analgesia" or "analgesic" is meant to include any conscious relief from a painful stimulus in an animal. In general, an analgesic is an agent that alleviates pain or reduces the sensation of pain without causing loss of consciousness. The term "long lasting" is generally meant to include the time interval from the onset of effect of the active until the effect has waned to a subclinical level. Thus, the establishment of this time interval is subjective but is readily ascertainable in the hands of the skilled artisan. Of course the duration of action of the active can vary, e.g., depending upon the route of administration, the species, age, size, and health status of the animal and the like. In the adult horse, for example, the clinical signs of sedation will begin to appear within 1–3 minutes following a single intravenous administration of about 100 mg of guanabenz or guanabenz acetate and the duration of action is up to about 4 hours.

The instant invention involves, in a preferred embodiment, methods for the administration of a novel veterinary composition comprising a guanidine derivative, e.g., guanabenz acetate, in a pharmacutically effective amount by intravenous, intramuscular, oral or other administration to produce a rapid onset and long lasting sedation and analgesia. The compositions provided by the present invention are designed to overcome the shortcomings of currently available veterinary sedatives, tranquilizers or analgesics and provide a more effective and longer lasting sedation and/or analgesia and/or means of chemical restraint, the effects of which may be rapidly reversed when desired.

In one embodiment, the present invention provides the surprising discovery that guanabenz acetate, after a single intravenous dose of about 0.2 milligrams per kilogram per horse, produces a rapid onset of sedation and/or, tranquilization and/or analgesia in the standing horse. After such a dose, profound sedation and head ptosis appear within one minute and is maintained for up to four hours which is of considerably longer longer duration than currently available α arenergic receptor agonists, e.g., xalazine and detomidine. This sedation and head ptosis response is rapidly reversible by intravenous administration of an alpha-2 adrenoceptor blocker (antagonist), e.g., yohimbine.

These sedation and analgesic responses can be associated with a hyperglycemic response which in turn causes an increased urine volume (diuresis) and a concomitant reduction in urine specific gravity. These pharmacological responses have not previously been described for guanabenz or other guanidine derivatives in the horse, and they show that this family of drugs has utility as a safe, effective long acting and rapidly reversible sedative, tranquilizer and analgesic in the horse.

In line with the foregoing, it is within the contemplation of the present invention to employ guanabenz or a guanidine derivative as a sedative, tranquilizer or analgesic. A derivative being qualified as a chemical substance derived from another substance either directly or by modification or partial substitution. It is important that the guanidine derivative possess the requesite α adrenergic receptor agonist activity. Examples of other suitable guanidine derivatives include but are not limited to:

Guanabenz-2-[(2,6-dichlorophenyl)methylene] hydrazinecarboximidamide

Guanadine sulfate-[2-(3,6-dihydro-4-methyl-1(2H)-pyridyl) ethyl]guanidine sulfate Guanadrel-(1,4-dioxaspiro[4,5]dec-2-ylmethyl)guanidine sulfate Guanacydine-N"-cyano-N-(1,1-dimethylpropyl)guanidine Guanethidine-[2-hexahydro-1(2H)-azocinyl)ethyl]guanidine Guanochlor sulfate-2-[2-(2,6-dichlorophenoxy)ethyl]hydrazine carboximidamide sulfate Guanoxabenz-2-[(2,6-dichlorophenyl)methylene]-N-hydroxyhydrazine carboximidamide Guanoxan sulfate-(2,3-dihydro-1,4-benzodioxin-2-ylmethyl)guanidine In a similar manner, salts (any compound of a base or an acid) as well as isomers (the possession by two or more distinct compounds of the same molecular formula, each molecule possessing an identical number of atoms of each element but in different arrangement) of the above mentioned compounds or other guanidine derivatives may be used in the compositions and methods provided by the invention. It is specifically contemplated that any pharmaceutically acceptable derivative of guanidine or the aforementioned compounds are within the scope of the invention as long as the derivative selected possesses sufficient α adrenergic receptor agonist activity.

The present compositions may be administered by routes well known to those skilled in veterinary medicine ant the related arts. Therefore, although the guanabenz for example, is conveniently administered intravenously, depending on the circumstances, the pharmaceutical composition may be administered, e.g., orally, intramuscularly, intravenously or by other routes known to those skilled in this art.

Compositions suitable for oral administration, include, e.g., suspensions, tablets, capsules, gels, pastes, boluses, or preparations in the form of powders, granules, or pellets. Presently preferred orally administered compositions according to the invention can include suspensions and tablets and paste formulations. Alternatively, and presently preferred, as set forth herein, the compositions of the invention may be formulated for parenteral administration, e.g., by intramuscular, intraperitoneal, or intravenous injection.

Pharmaceutically acceptable carriers present in the compositions of the present invention are materials recommended for the purpose of administering the medicament in the desired dosage form. These may be liquid, solid, or gaseous materials, which are otherwise inert or medically acceptable and are compatible with the active ingredients. The same applies for any added excipients, solvents of the active, buffers, preservatives and the like.

For oral administration, fine powders or granules may contain diluting agents, for example, calcium carbonate, calcium phosphate, mineral carriers, etc., disbursing and/or surface active agents, for example, polysorbates, and may be presented in a drench, in water or in a syrup, in a bolus, paste, or in capsules or sachets in the dry state or in a non-aqueous suspension, or in a suspension in water or syrup. Intravenous and intramuscular preparations may, e.g., include suitable solvents of the active and can include buffering agents, preservatives and the like.

Where desirable or necessary, preserving, suspending, thickening or emulsifying agents can be included. If intended for oral use, a bolus can be provided for large animals with retention means to inhibit regurgitation. For example, it may be weighed with a heavy density materials such as iron or tungsten or the like or may be retained by its shape, for example, by wings which spring after administration. Boluses may contain disintegrating agents such as maize starch or calcium or sodium methylcelluloses, hydroxypropylmethylcellulose, guar based vegetable gums, sodium alginates or sodium starch glycolates; granulating or binding agents, such as starch in the form of mucilage, starch derivatives, such as methylcellulose, calcium stearate, talc, gelatin or polyvinylpyrrolidone; and/or lubricating agents, such as magnesium stearate or stearic acid.

Other compounds which may be included are, for example, medically inert ingredients, e.g. solid and liquid diluents, such as starch or calcium phosphate for tablets, boluses or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; dedusting agents such as liquid paraffin, fixed oils and surfactants and other therapeutically acceptable accessory ingredients, such as humectants, preservatives, buffers, and anti-oxidants, which are useful as carriers in such formulations. When desired, other medicaments and/or nutrients, unless contraindicated, may also be included.

It is also to be understood that while the preferred formulation is formulated in unit dosage form for a single administration, alternatively, the compositions of the invention may be given to effect (to achieve a desired level of sedation and/or analgesia), administered in divided doses, or supplemental doses administered as needed.

In particular, one embodiment of the present invention provides a veterinary composition comprising a pharmaceutically effective amount of a pharmaceutically acceptable guanidine derivative which is useful for providing a rapid onset and long lasting analgesia and/or sedation in an animal. As set forth above, the guanidine derivative can be any of the afore-mentioned compounds or other derivatives of guanidine provided that the selected active possesses sufficient α adrenergic receptor agonist activity to be used in accordance with the methods of the invention and provided that the selected active does not produce unwanted side effects in the subject animal which will affect the long term health of the animal.

In a preferred embodiment, the invention provides a composition wherein the guanidine derivative is selected from the group consisting of guanabenz, guanabenz acetate, guanoxabenz, clonidine, guanacline, guanadrel, guanazodine, guanethidine, guanfacine and guanochlor, guanoxan, and mixtures thereof. In yet another embodiment, the preferred guanidine derivative is guanabenz, guanabenz acetate or pharmaceutically acceptable derivatives thereof.

Of course, one of skill in the art can appreciate that the compositions of the invention can further comprise a pharmaceutically acceptable carrier and specific embodiments thereof are hereby provided. Likewise, the present invention provides specific embodiments wherein the veterinary composition comprised of a pharmaceutically effective amount of a guanidine derivative is specially adapted for oral, intramuscular or intravenous administration. As set forth above, it can be appreciated by the skilled artisan that the compositions set forth herein can be formulated for and adapted for use in any species of animal, including, but not limited to equine, canine, feline, bovine, caprine, porcine and ovine species.

In one preferred embodiment, the invention provides a veterinary composition comprising a pharmaceutically effective amount of a guanidine derivative, e.g., guanabenz or guanabenz acetate, which useful for providing a rapid onset and long lasting analgesia and sedation in a standing animal, e.g., a horse. As set forth in the examples below, the rapid onset and lasting duration of a single intravenous administration of the active provides a novel and heretofore unreported use for this family of compounds.

A particularly attractive feature of the compositions provided by the invention is that the analgesia and sedation produced by administration of the active are rapidly reversible. In particular, one embodiment of the invention provides a method for selective reversal of the analgesic, and/or tranquil and/or sedative effects via administration of a pharmaceutically effective amount of an α adrenergic antagonist. Examples of suitable α adrenergic antagonists, include but are not limited to yohimbine, rauwolscine, idazoxan, tolazoline and atepamezole.

In a presently preferred embodiment, the α adrenergic antagonist suitable for reversal of the active is yohimbine or tolazoline. A presently preferred dosage of yohimbine for reversal of the active guanidine derivative is between about 0.04 to about 0.08 mg/kg I.V. and the preferred dosage of tolazoline is between about 2.0 to about 4.0 mg/kg I.V. One of skill in the art can appreciate that the dosage of the reversal agent will vary depending upon, e.g., the length of time from administration of the active, the dosage and route of administration, the species of animal, size and health of the animal and the like.

In a presently preferred embodiment, the invention provides a veterinary composition comprised of a pharmaceutically effective amount of a guanidine derivative that is useful for providing a rapid onset and long lasting analgesia and sedation in an animal wherein the pharmaceutically effective amount is between about 0.05 mg/kg and about 0.50 mg/kg. The compositions of the invention can be formulated in unit dosage form, e.g., in an oral tablet formulated on a preferred administration rate for a particular species of animal or in injectaable an form, e.g., the selected active in a 1 mg/ml solution. In a presently preferred embodiment, the pharmaceutically effective amount of the quanidine derivative is about 0.25 mg/kg. In a particularly preferred embodiment the compositions of the invention are comprised of a guanidine derivative that is guanabenz, guanabenz acetate or a pharmaceutically acceptable derivative thereof and the pharmaceutically effective amount is between about 0.05 mg/kg and about 0.50 mg/kg, but is especially about 0.25 mg/kg.

The present invention also provides for methods of inducing a rapid onset and long lasting sedation and/or analgesia in an animal. The methods comprise administering to the animal a pharmaceutically effective amount of a composition comprised of a guanidine derivative. As set forth above with reference to the compositions of the invention, the guanidine derivative can be any derivative of the guanidine family so long as the selected derivative possesses the requisite α adrenergic receptor agonist activity to produce the desired clinical effects in the animal without causing undue side effects. Examples of suitable guanidine derivatives include, but are not limited to guanabenz, guanabenz acetate, guanoxabenz, clonidine, guanacline, guanadrel, guanazodine, guanethidine, guanfacine and guanochior, guanoxan and mixtures thereof. The presently preferred methods of the invention comprise of inducing a rapid onset and long lasting sedation and/or analgesia in an animal. The methods comprise administering to the animal a pharmaceutically effective amount of guanabenz, guanabenz acetate or pharmaceutically acceptable derivatives thereof.

One of skill in the art will appreciate that the administering step provided by the invention can be via any route, including but not limited to oral, intravenous and intramuscular. Further, the methods provided herein are contemplated for use on any animal, including but not limited to equine, canine, feline, bovine, caprine, porcine and ovine. In a particularly preferred embodiment of the methods of the invention the animal is a large animal, e.g., a horse or a cow, and the sedation and analgesia are induced and maintained while the animal is standing.

The compositions comprised of guanidine derivatives administered according to the methods of the invention are administered in pharmaceutically effective amounts which can range from between about 0.05 mg/kg and about 0.50 mg/kg of the active. In one preferred embodiment, the pharmaceutically effective amount of the guanidine derivative is about 0.25 mg/kg.

A presently preferred method of the invention, comprises inducing a rapid onset and long lasting sedation and/or analgesia in an animal, comprising administering to the animal a pharmaceutically effective amount of a composition comprised of guanabenz, guanabenz acetate or pharmaceutically acceptable derivatives thereof and wherein the pharmaceutically effective amount is between about 0.05 mg/kg and about 0.50 mg/kg but is especially about 0.25 mg/kg.

Of particular importance with respect to the methods for providing long lasting sedation and/or tranquilization and/or analgesia set forth herein is the fact that the method further provides the ability for selectively reversing or controlling the level of analgesia and/or sedation and/or tranquilization in the animal. The methods of the invention can therefore further comprise the step administering a pharmaceutically effective amount of α adrenergic receptor antagonist to the animal to control or reverse the effects of the previously administered α adrenergic receptor agonists. The α adrenergic receptor antagonists suitable for use in the invention include, but are not limited to yohimbine, rauwolseine, idazoxan and atepamezole. Presently preferred α adrenergic receptor antagonists are yohimbine or tolazoline. A presently preferred dosage of yohimbine for reversal of the active guanidine derivative administered according to the methods set forth herein is between about 0.04 to about 0.08 mg/kg I.V. and the preferred dosage of tolazoline is between about 2.0 to about 4.0 mg/kg I.V. One of skill in the art can appreciate that the dosage of the reversal agent will vary depending upon, e.g., the length of time from administration of the active, the dosage and route of administration, the species of animal, size and health of the animal and the like.

One of skill in the art can also appreciate that the compositions and methods of the invention have many applications and uses in the field of veterinary medicine. In addition to providing a means for chemical restraint of animals, particularly large animals, the compounds may be used in situations whenever analgesia and/or sedation are required. In the equine species for example, the compositions of the invention may be used to treat any source of pain but may be especially useful in alleviating or lessening the pain associated with colic (abdominal pain). Likewise, the pain assocaited with acute racing injury and/or post surgical pain may be treated via the compositions disclosed herein.

A further appreciation of the invention may be gleaned from the following specific examples. These specific examples are provided for illustration only and are not to be regarded as restricting the invention in any way.

EXAMPLES

Example 1

Guanabenz Produces a Rapid Onset of Tranqulization and Sedation:

As shown in FIG. 1, a horse (about 1000 lbs), was administered guanabenz at a dose of 0.2 mg/kg (100 mg) intravenously at time point 0. Note how the dose of 100 mg of guanabenz yields a very rapid onset of analgesia response as indicated by the decrease in head ptosis of the horse. The solid circles (● - - - ●) show head ptosis measured as cm above ground level after rapid intravenous administration of guanabenz. Note also the rapid reversal of this tranquilization and sedation by the administration of yohimbine (see arrow) at a dose of 60 mg intravenously. The open circles (○ - - - ○) show the rapid reversal effect by intravenous injection of yohimbine.

The advantages of this approach are many fold: In the first place, effective sedative and tranquilizing levels of guanabenz or a derivative thereof are attained within minutes of the administration of the compound, which leads to shorter waiting time to initiate desired procedure or treatment. In the second place, the animal will remain in a standing position. Thirdly, the duration of the sedation and tranquilization lasts for an extended period of time, enabling the performance of lengthier procedures or treatments. Fourthly, the sedative and tranquilizing effect of guanabenz or derivatives thereof can be rapidly reversed by the administration of yohimbine or any other alpha-2-adreno receptor antagonist.

Example 2

Figure 2:
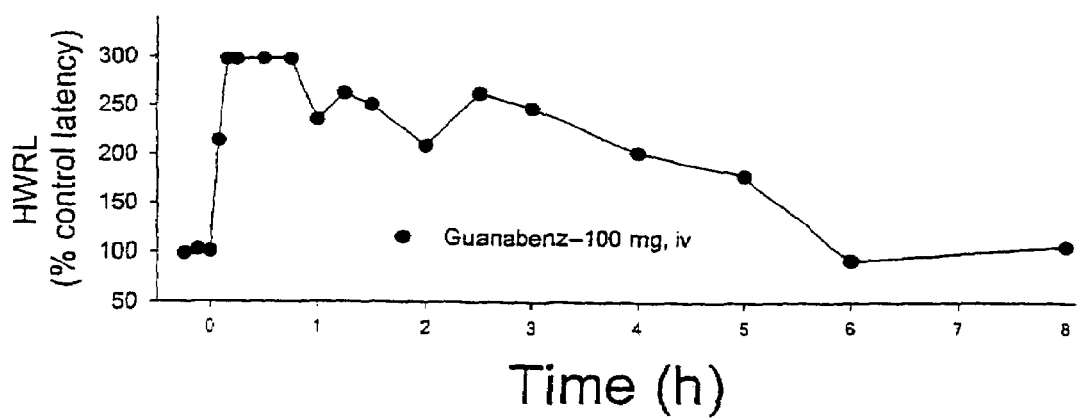
FIG. 2 is a plot of rapid onset of analgesia response in a horse following administration of intravenous guanabenz (100 mg, 0.2 mg/kg)

Analgesic Response to Guanabenz in the Horse:

A horse (1000 lbs) in was administered guanabenz at a dose of 0.2 mg/kg (100 mg) intravenously at time point 0 (see FIG. 2). Note how the dose of 100 mg of guanabenz yields a very rapid onset of analgesia response as indicated by the increase in desensitization to the heat lamp. Note also that this response is maintained at full intensity for approximately 30 minutes and declines thereafter, and returns to control values by 6 hrs post administration. The solid circles (● - - - ●) show the increasing control latency in our heat lamp equine analgesia model after administration of guanabenz at indicated zero time.

Example 3

Figure 3:
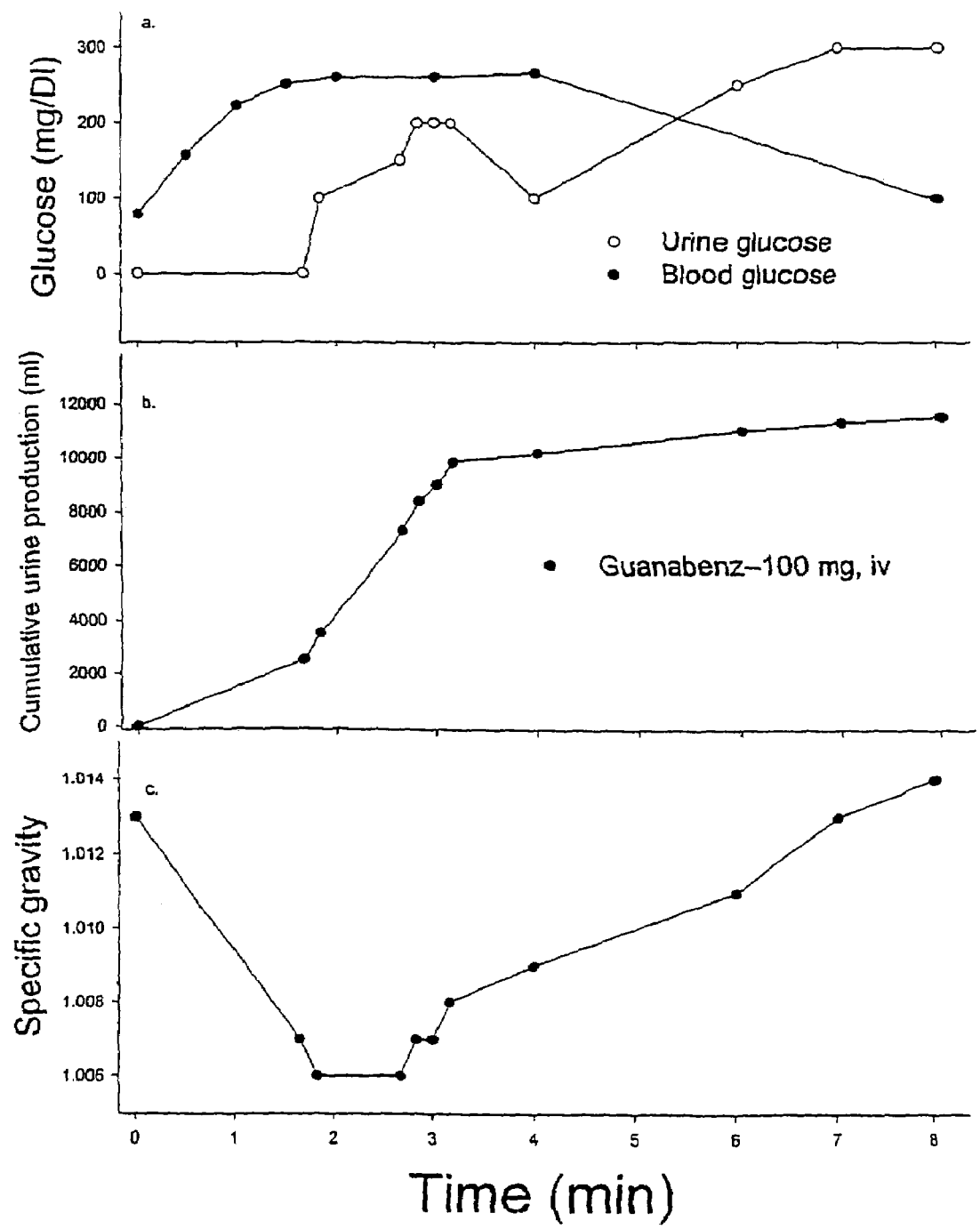
FIG. 3 plots, in a horse administered intravenous guanabenz (100 mg, 0.2 mg/kg), (a) blood glucose levels (mg/Dl); (b) urine production (ml); and (c) urine specific gravity.

Guanabenz IV Produces a Transient Diuresis with a Corresponding Reduction in Urinary Specific Gravity and Transient Hyperglycemia and Glucosuria:

Referring now to FIG. 3, a horse (about 1000 lbs) was administered guanabenz at a dose of 0.2 mg/kg (100 mg) intravenously at time point 0. In FIG. 3a, note how the dose of 100 mg of guanabenz yields a transient increase in blood glucose levels after the administration of guanabenz. The solid circles (● - - - ●) show blood glucose levels after rapid intravenous administration of guanabenz. Note also the increase in urine glucose levels after the administration of guanabenz. The open circles (○-○) show the corresponding urinary concentrations of glucose after this administration.

In FIG. 3b, note how the dose of 100 mg of guanabenz yields an increase in urine production as indicated by the increase in volume of urine collected. The solid circles (● - - - ●) show volume of urinary output after rapid intravenous administration of guanabenz. Note also in FIG. 3c, the decrease in specific gravity of the urine after the administration of the guanabenz. The solid circles (● - - - ●) show the corresponding urinary specific gravity values after this administration.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application thereby enable one of ordinary skill in the art to utilize the invention in various embodiments and with various modifications and variations are within the scope of the invention as determined by the appended claims when interpreted in accordance with the breadth to which they are fairly, legally and equitable entitled.

What is claimed is:

1. A method of inducing rapid onset and long lasting sedation and analgesia in an animal, comprising administering to the animal a pharmaceutically effective amount of a composition consisting essentially of a guanidine derivative selected from the group consisting of guanabenz, guanabenz acetate, guanoxabenz, clonidine, guanacline, guanadrel, guanazodine, guanethidine, guanfacine, guanochior, and guanoxan.

2. The method of claim 1, wherein the guanadine derivative is guanabenz acetate or pharmaceutically acceptable derivative thereof.

3. The method of claim 1, wherein the administration is oral.

4. The method of claim 1, wherein the administration is intravenous.

5. The method of claim 1, wherein the administration is intramuscular.

6. The method of claim 1, wherein the animal is selected from the group consisting of equine, canine, feline, bovine, caprine, porcine and ovine.

7. The method of claim 1, wherein the animal is an equine.

8. The method of claim 1 wherein the rapid onset sedation and analgesia is induced in a standing animal.

9. The method of claim 1, further comprising the step of selectively reversing or controlling the level of analgesia and sedation in the animal comprising administering a pharmaceutically effective amount of α adrenergic antagonist to the animal.

10. The method of claim 9 wherein the α adrenergic antagonist is selected from the group consisting of yohimbine, rauwolscine, idazoxan and atepamezole.

11. The method of claim 1, wherein the pharmaceutically effective amount of the guanidine derivative is between about 0.05 mg/kg and about 0.50 mg/kg.

12. The method of claim 1, wherein the pharmaceutically effective amount of the guanidine derivative is about 0.25 mg/kg.

13. The method of claim 1, wherein the guanidine derivative is guanabenz acetate or a pharmaceutically acceptable derivative thereof and the pharmaceutically effective amount is between about 0.05 mg/kg and about 0.50 mg/kg.

14. The method of claim 1, wherein the guanidine derivative is guanabenz acetate or a pharmaceutically acceptable derivative thereof and the pharmaceutically effective amount is about 0.25 mg/kg.

15. The method of claim 1, wherein the guanidine derivative is an α adrenergic agonist.

* * * * *

UNITED STATES PATENT AND TRADEMARK OFFICE
CERTIFICATE OF CORRECTION

PATENT NO. : 7,074,834 B2  Page 1 of 1
APPLICATION NO. : 09/865175
DATED : July 11, 2006
INVENTOR(S) : Tobin It is certified that error appears in the above-identified patent and that said Letters Patent is hereby corrected as shown below:

On The Title Page:

Item (73) Assignee: should read --University of Kentucky Research Foundation, Lexington, KY (US) --.

Signed and Sealed this

Nineteenth Day of September, 2006

JON W. DUDAS
*Director of the United States Patent and Trademark Office*